(12) United States Patent
Guo et al.

(10) Patent No.: US 6,960,323 B2
(45) Date of Patent: *Nov. 1, 2005

(54) COMPOSITIONS CONTAINING A UREA DERIVATIVE DYE FOR DETECTING AN ANALYTE AND METHODS FOR USING THE SAME

(75) Inventors: Sherry X. Guo, San Jose, CA (US); Koon-wah Leong, Sunnyvale, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/732,389

(22) Filed: Dec. 9, 2003

(65) Prior Publication Data

US 2004/0121423 A1 Jun. 24, 2004

Related U.S. Application Data

(62) Division of application No. 09/593,827, filed on Jun. 13, 2000, now Pat. No. 6,743,597.

(51) Int. Cl.$^7$ .............................................. G01N 21/00
(52) U.S. Cl. ........................................ 422/60; 435/28
(58) Field of Search ............................ 422/60; 435/28; 436/904

(56) References Cited

U.S. PATENT DOCUMENTS

| | | | |
|---|---|---|---|
| RE30,267 E | | 5/1980 | Bruschi |
| 5,362,633 A | | 11/1994 | Pugia |
| 5,445,944 A | | 8/1995 | Ullman |
| 5,972,294 A | * | 10/1999 | Smith et al. .................. 422/58 |
| 6,743,597 B1 | * | 6/2004 | Guo et al. .................... 435/14 |

FOREIGN PATENT DOCUMENTS

| | | |
|---|---|---|
| EP | 0038205 | 10/1981 |
| EP | 0124827 | 11/1984 |
| EP | 0251297 | 1/1988 |
| EP | 0555045 | 8/1993 |
| JP | 09019296 | 1/1981 |
| JP | 0118768 | 5/1989 |
| WO | WO 97/39142 | 10/1997 |

OTHER PUBLICATIONS

Yagi, et al., "Use of a New Methylene Blue Derivative for Determination of Lipid Peroxides in Foods", Biochemistry International, vol. 12, No. 2, Feb. 1986, pp. 367–371.

* cited by examiner

*Primary Examiner*—Ralph Gitomer
(74) *Attorney, Agent, or Firm*—Carol M. LaSalle; Bozicevic, Field & Francis LLP

(57) ABSTRACT

Compositions, reagent test strips, analyte detection systems and kits of the same, as well as methods for their use in the detection of an analyte in a sample, are provided. The subject compositions are characterized by having a positively charged porous matrix and a urea derivative dye on at least one surface of the matrix, where in many preferred embodiments the urea derivative dye is a negatively charged urea derivative dye. In many preferred embodiments, the subject compositions further include at least one additional reagent member of a peroxide producing signal producing system, e.g., an analyte oxidase and/or a peroxidase. The subject compositions, test strips, analyte detection systems and kits find use in the detection of a wide variety of analytes in a sample, such as a physiological sample, e.g., blood or a fraction thereof.

3 Claims, 3 Drawing Sheets

COMPOSITIONS CONTAINING A UREA DERIVATIVE DYE FOR DETECTING AN ANALYTE AND METHODS FOR USING THE SAME

CROSS REFERENCES

This application is a divisional application of U.S. patent application Ser. No. 09/593,827, filed Jun. 13, 2000, now issued U.S. Pat. No. 6,743,597.

INTRODUCTION

1. Field of the Invention

The field of this invention is analyte detection, particularly reagent systems for use in analyte detection.

2. Background of the Invention

Analyte detection in physiological fluids, e.g., blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose, alcohol, formaldehyde, L-glutamic acid, glycerol, galactose, glycated proteins, creatinine, ketone body, ascorbic acid, lactic acid, leucine, malic acid, pyruvic acid and uric acid, steroids, etc. In response to this growing importance of analyte detection, a variety of analyte detection protocols and devices for both clinical and home use have been developed.

Many of the protocols and devices that have been developed to date employ a signal producing system to identify the presence of the analyte of interest in a physiological sample, such as blood. One type of signal producing system that finds use in the detection of a variety of different analytes is one in which an oxidase or a peroxidase enzyme oxidizes the analyte of interest and produces hydrogen peroxide. The hydrogen peroxide is then detected by subsequent enzyme-catalyzed reaction with a dye substrate to produce a detectable chromogenic product. Dyes useful in such signal producing systems generally yield a visible color signal with high sensitivity.

A variety of highly sensitive dyes are commonly used in peroxide producing signal producing systems. However, many highly sensitive dyes such as urea derivative dyes are limited by their stability (e.g., to oxidation, light) in the solid phase and/or in solution.

While compositions containing highly sensitive dyes have been developed, there continues to be a need for the further development of such compositions. For example, solid phase compositions that include highly sensitive urea derivative dyes and are resistant to oxidation would be of great interest.

Relevant Literature

Patents of interest include: JP 1118768; JP 9019296; EP 38 205, EP 124 287 and EP 251297. See also, Yagi et al. (1986) *Biochem. Int.* 12:367–371.

SUMMARY OF THE INVENTION

Compositions, reagent test strips, analyte detection systems and kits of the same, as well as methods for their use in the detection of an analyte in a sample, are provided. The subject compositions are characterized by having a positively charged porous matrix and a urea derivative dye on at least one surface of the matrix, where in many preferred embodiments the urea derivative dye is a negatively charged urea derivative dye. In many preferred embodiments, the subject compositions further include at least one additional reagent member of a peroxide producing signal producing system, e.g., an analyte oxidase and/or a peroxidase. The subject compositions, test strips, analyte detection systems and kits find use in the detection of a wide variety of analytes in a sample, such as a physiological sample, e.g., blood or a fraction thereof.

DESCRIPTION OF THE SPECIFIC EMBODIMENTS

Figure 1:
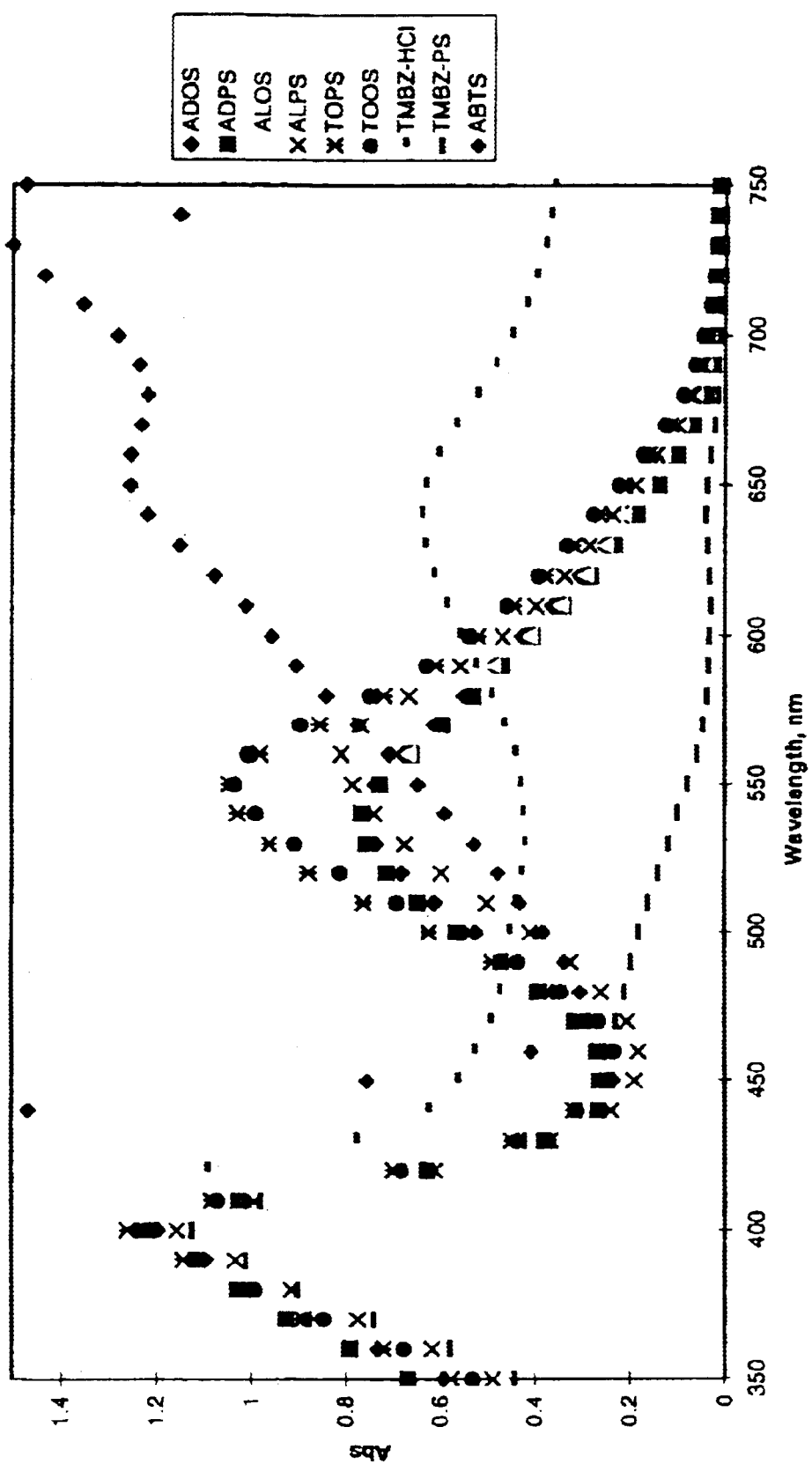
FIGS. 1 and 2 provide a graphical representation of the UV absorbance of various commercially available dye substrates (1 mM) after reacting with horseradish peroxidase (1 mg/mL, 549 U/mg) and hydrogen peroxide (50 $\mu$M) in pH 7.4 PBS buffer (0.02 M).
Figure 2:
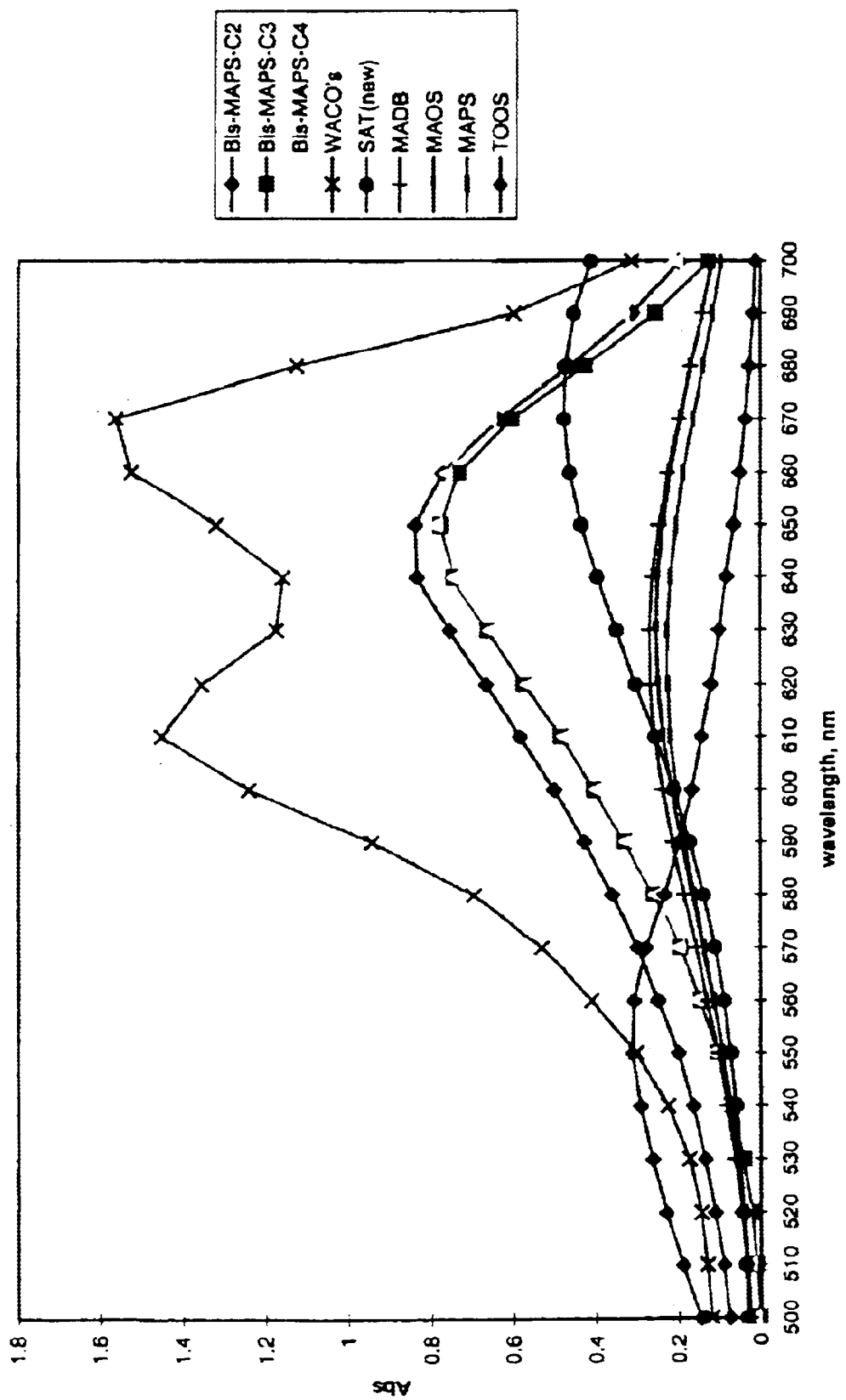

Compositions, reagent test strips, analyte detection systems and kits of the same, as well as methods for their use in the detection of an analyte in a sample, are provided. The subject compositions are characterized by having a positively charged porous matrix and a urea derivative dye on at least one surface of the matrix, where in many preferred embodiments the urea derivative dye is a negatively charged urea derivative dye. In many preferred embodiments, the subject compositions further include at least one additional reagent member of a peroxide producing signal producing system, e.g., an analyte oxidase and/or a peroxidase. The subject compositions, test strips, analyte detection systems and kits find use in the detection of a wide variety of analytes in a sample, such as a physiological sample, e.g., blood or a fraction thereof. In further describing the subject invention, the subject compositions are discussed first, followed by a review of representative applications in which the compositions find use and systems and kits that include the subject compositions.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Compositions and Reagent Test Strips

As summarized above, the subject invention provides compositions for use in detecting a wide variety of analytes in a sample. The compositions include a positively charged porous matrix and a urea derivative dye on at least one surface of the matrix. In many embodiments, however, the compositions further include at least one additional reagent member of a peroxide producing signal producing system, and typically include a plurality of signal producing system members: The reagent compositions are dry compositions, such as are typically found in reagent test strips. In particular, the invention provides strips for assaying for a particular analyte in whole blood, e.g., glucose, alcohol, glycated proteins, etc. In the broadest sense, the reagent test strips include a positively charged porous matrix and a peroxide producing signal producing system present on said matrix, which system includes a urea derivative dye. In most embodiments, the signal producing system present on said matrix further includes an analyte oxidizing enzyme.

The above elements are now further described in greater detail.

Positively Charged Porous Matrix

The matrix that is employed in the subject test strips is an inert porous matrix which provides a support for the various members of the signal producing system, described infra, and has a positive charge. The matrix is configured to provide a location for application of a physiological sample, e.g., blood, and detection of the chromogenic product produced by the dye of the signal producing system. As such, the matrix is one that is permissive of aqueous fluid flow through it and provides sufficient void space for the chemical reactions of the signal producing system to take place. A number of different positively charged porous matrices have been developed for use in various analyte detection assays, which matrices may differ in terms of materials, pore sizes, dimensions and the like, where representative matrices include those described in U.S. Pat. Nos. 55,932,431; 5,874,099; 5,871,767; 5,869,077; 5,866,322; 5,834,001; 5,800,829; 5,800,828; 5,798,113; 5,670,381; 5,663,054; 5,459,080; 5,459,078; 5,441,894 and 5,212,061; the disclosures of which are herein incorporated by reference. The dimensions and porosity of the test strip may vary greatly, where the matrix may or may not have a porosity gradient, e.g., with larger pores near or at the sample application region and smaller pores at the detection region. Positively charged membranes can be prepared by using positively charged polymers, such as polyamide. Alternatively, such membranes can be prepared by various techniques, such as surface coating using cationic surfactants or polymers. The coating can be applied by dip coating, chemical treatment, photografting, plasma polymerization, etc. In yet other embodiments, the membrane can be prepared by means of blending one or more positively charged material with the membrane forming polymer. Examples of positively charged polymers are polyamide, poly(vinyl pyridine), poly(vinyl imidazole), poly(allylamine), poly(vinyl benzyldimethyl ammonium chloride), polylysine. Examples of cationic surfactants include those containing primary, secondary and quaternary amino groups. The material may or may not be functionalized to provide for covalent or noncovalent attachment of the various members of the signal producing system, described in greater detail infra.

In many embodiments, the matrix is configured as a membrane test pad and is affixed to a solid support, where the support may be a plastic (e.g., polystyrene, nylon or polyester) or metallic sheet or any other suitable material known in the art. Of interest in many embodiments are the test strip configurations disclosed in U.S. Pat. Nos. 5,972,294; 5,968,836; 5,968,760; 5,902,731; 5,846,486; 5,843,692; 5,843,691; 5,789,255; 5,780,304; 5,753,452; 5,753,429; 5,736,103; 5,719,034; 5,714,123; 383,550; 381,591; 5,620,863; 5,605,837; 5,563,042; 5,526,120; 5,515,170; 367,109; 5,453,360; 5,426,032; 5,418,142; 5,306,623; 5,304,468; 5,179,005; 5,059,394; 5,049,487; 4,935,346; 4,900,666 and 4,734,360, the disclosures of which are herein incorporated by reference.

Signal Producing System

In addition to the positively charged porous matrix, the subject test strips further include one or more members of a signal producing system which produces a detectable product in response to the presence of analyte, which detectable product can be used to derive the amount of analyte present in the assayed sample. In the subject test strips, the one or more members of the signal producing system are associated, e.g., covalently or non-covalently attached to, at least a portion of (i.e., the detection region) the positively charged porous matrix, and in many embodiments to substantially all of the positively charged porous matrix.

The signal producing system is an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product produced by the signal producing system, i.e., the signal, is then related to the amount of analyte in the initial sample. As such, the analyte oxidation signal producing systems present in the subject test strips are also correctly characterized as hydrogen peroxide based signal producing systems or peroxide producing signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the enzyme may be: glucose oxidase (where the analyte is glucose); cholesterol oxidase (where the analyte is cholesterol); alcohol oxidase (where the analyte is alcohol); formaldehyde dehydrogenase (where the analyte is formaldehyde), glutamate oxidase (where the analyte is L-glutamic acid), glycerol oxidase (where the analyte is glycerol), galactose oxidase (where the analyte is galactose), a ketoamine oxidase (where the analyte is a glycated protein, e.g., fructosamine), a 3-hydroxybutyrate dehydrogenase (where the analyte is a ketone body), L-ascorbate oxidase (where the analyte is ascorbic acid), lactate oxidase (where the analyte is lactic acid), leucine oxidase (where the analyte is leucine), malate oxidase (where the analyte is malic acid), pyruvate oxidase (where the analyte is pyruvic acid), urate oxidase (where the analyte is uric acid oxidase) and the like. Other oxidizing enzymes for use with these and other analytes of interest are known to those of skill in the art and may also be employed.

The signal producing systems also include an enzyme that catalyzes the conversion of a dye substrate into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Ci et al. (1990) *Analytica Chimica Acta*, 233:299–302.

The dye substrates are oxidized by hydrogen peroxide in the presence of the peroxidase to produce a product that absorbs light in a predetermined wavelength range, i.e., an indicator dye. Preferably the indicator dye absorbs strongly at a wavelength different from that at which the sample or the testing reagent absorbs strongly. The oxidized form of the indicator may be the colored, faintly-colored, or colorless final product that evidences a change in color of the testing side of the membrane. That is to say, the testing reagent can indicate the presence of an analyte in a sample by a colored area being bleached or, alternatively, by a colorless area developing color.

Dye substrates that are useful in the present invention include urea derivative dyes. Urea derivative dyes include at least some of those disclosed in JP 1118768; JP 9019296; EP 38 205, EP 124 287 and EP 251297; the disclosures of which are herein incorporated by reference. The dye substrate is generally a urea derivative, having a negative charge, where suitable negatively charged urea derivatives include those bearing a carboxylate group or a sulfonate group. Urea derviative dyes of interest are represented by the following formula:

wherein
$R^1$, $R^2$ taken together is a N,N-di-substituted aminoaryl; and
$R^3$ is selected from the group consisting of carboxyalkyl, alkoxycarbonyl, alkylcarbonyl, arylsulfonyl, sulfoaryl and carboxyaryl.

The aryl groups of $R^1$ and $R^2$ may be bonded via S to become a phenothiazine derivative type of dye, which is represented by the following formula:

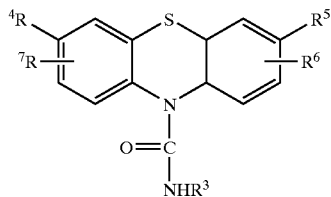

wherein $R^4$ and $R^5$ are independently selected from $NR_2$ and OR, where R is hydrogen, $(C_1-C_6)$-alkyl, $(C_1-C_6)$-alkenyl, aryl, substituted aryl, arylalkyl, substituted arylalkyl; $R^3$ is defined above; and $R^6$ and $R^7$ are independently selected from hydrogen, $(C_1-C_6)$-alkyl, $(C_1-C_6)$-alkenyl, acyl, carboxyl, sulfonyl, nitro, halogen, hydroxyl, $(C_1-C_6)$-alkoxyl or hydroxy-$(C_1-C_6)$-alkyl.

Alternatively, the aryl groups of $R^1$ and $R^2$ may be bonded via O, to form a phenoxazine derivative type of dye, which is represented by the following formula:

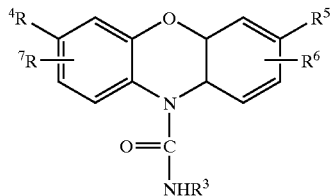

In yet another embodiment, the aryl groups of $R^1$ and $R^2$ is not bonded, which is represented by the following diphenylamine formula:

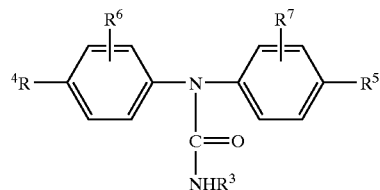

Exemplary urea derivative dyes include 10-(carboxymethylaminocarbonyl)-3,7-bis(dimethylamino) phenothiazine (leuco methylene blue), 10-(carboxymethylaminocarbonyl)-4,4'-bis(dimethylamino) diphenylamine, 10-propionic acid phenothiazine, and salts thereof. In a preferred embodiment, the urea derivative dye is 10-(carboxymethylaminocarbonyl)-3,7-bis(dimethylamino)phenothiazine, sodium salt.

Because of the nature of the composition, the urea derivative dye component of the composition is stable, i.e., resistant to decomposition by oxidation, as compared to the solution state, especially the aqueous solution state. As such, the subject compositions can be stored under various temperature and humidity conditions with no observable change in color, i.e., the subject compositions are storage stable. Representative conditions under which the subject compositions and reagent test strips are storage stable include in the experimental section, infra. Based on these findings, the subject compositions are stable at temperatures ranging from about at least about −80° C. to 60° C., usually from about −20° C. to 56° C. under humidity ranging from at least about 0% to 80%, usually from about 5% to 20% for periods of time ranging from at least about six months to one and a half year, usually from about nine months to one year. The subject compositions are more stable than compositions that include a neutral or negatively charged porous matrix, e.g., a hydrophilic polysulfone membrane or cellulose filter paper, where the magnitude of this increased stability is at least about one hundred fold.

The subject reagent test strips may be fabricated employing any convenient protocol. One convenient protocol is to first contact at least the test pad portion of the strip with an aqueous solution that includes all of the members of the reagent composition that are to be associated with the test pad in the final reagent test strip except the urea derivative dye. Conveniently, the test pad may be immersed in the aqueous solution, maintained therein for a sufficient period of time and then dried. The test pad may subsequently be immersed in an organic solution, e.g., a 70% methanol solution, that includes the urea derivative dye, maintained therein for a sufficient period of time and then dried, whereby the test pad of the reagent test strip which has associated therewith the composition is produced.

As stated above, the aqueous solution will include various members of the composition to be associated with the test pad of the reagent test strip except the urea derivative dye and the organic solution will include the urea derivative dye member where all members are present in amounts sufficient to provide for the desired amounts in the reagent composition that is produced on the test pad. As such, the concentration of the analyte oxidase typically ranges from about $5 \times 10^{-3}$ to 0.25 mM, usually from about 0.05 to 0.10 mM. Similarly, the peroxidase ranges in concentration from about $5 \times 10^{-4}$ to 0.125 mM, and usually from about 0.005 to 0.05 mM, when present. The concentration of the urea derivative dye typically ranges from about 0.5 to 2 mM, usually from about 0.8 to 1.2 mM. Other components that may be present in the aqueous solution employed to prepare the reagent test strip include sodium chloride, magnesium chloride, Tris, PSSA, TECTRONIC® 1307 non-ionic surfactant (sold by BASF Corn.), crotein, sucrose, oxamic acid, sodium salt, EDTA, mannitol, polymers such as PVP and PVBTA, and the like. See the examples section, infra, for a more detailed description of a representative method for preparing the subject reagent test strips.

Methods of Analyte Detection

The above described compositions, reagent test strips and signal producing systems find use in methods of detecting the presence of, and often the amount of, an analyte in a sample. A variety of different analytes may be detected using the subject methods, where representative analytes include those described above, e.g., glucose, alcohol, formaldehyde, L-glutamic acid, glycerol, galactose, glycated proteins, creatinine, ketone body, ascorbic acid, lactic acid, leucine, malic acid, pyruvic acid, uric acid, and steroids, etc. While in principle, the subject methods may be used to determine the presence, and often concentration, of an analyte in a variety of different physiological samples, such as urine, tears, saliva, and the like, they are particularly suited for use in determining the concentration of an analyte in blood or blood fractions, e.g., blood derived samples, and more particularly, in whole blood.

Figure 3:
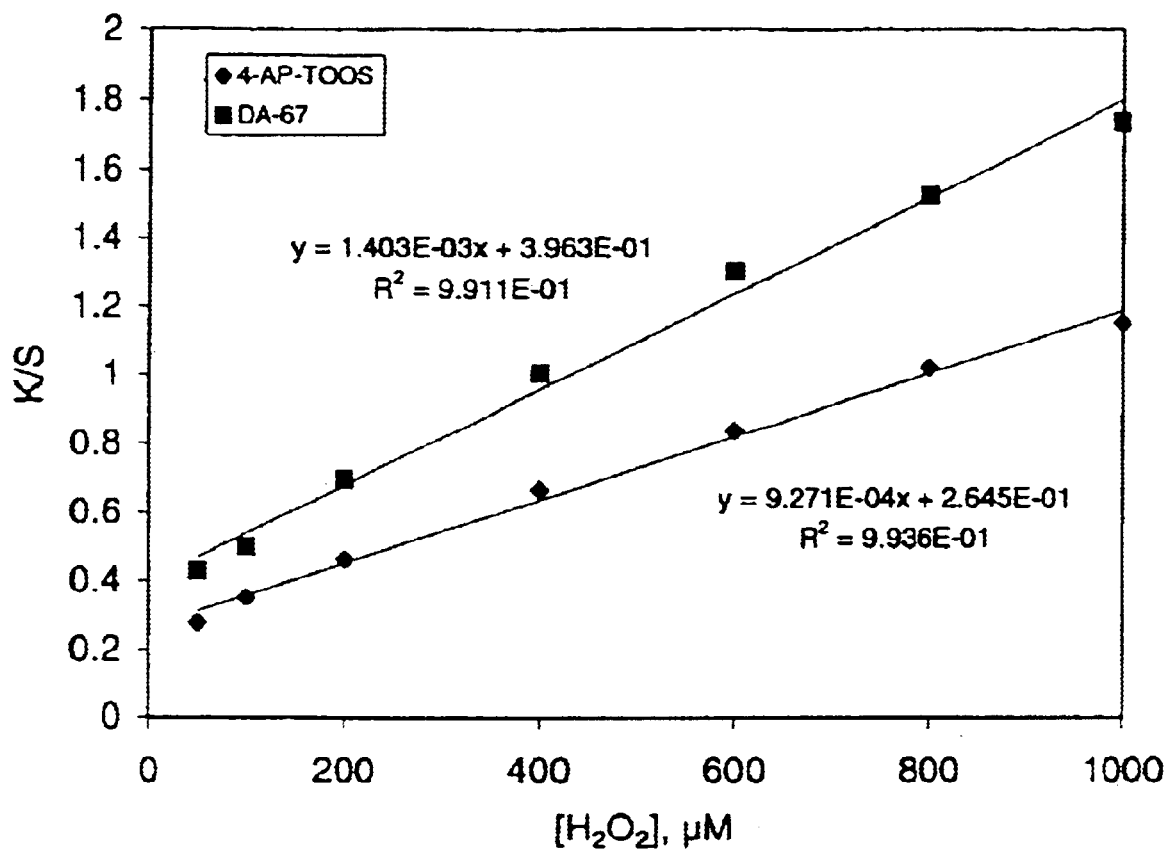
FIG. 3 provides a graphical representation of the effects of hydrogen peroxide concentration on DA-67 and TOOS-4 AP coated ONE-TOUCH® nylon membranes. TOOS-4 AP strips were coated with a 0.02 M PBS, pH 7.4 solution containing 5 mM TOOS and 4 AP respectively, 1 mg/ml HRP and 1% PVP (360 K). The DA-67 strips were coated with 2.5 mM DA-67, 1 mg/ml HRP, 1% PVP(360 K) in 0.5 M pH 8.0 phosphate buffer

An important feature of the subject methods is that use of the subject signal producing systems that include a urea derivative dye provides for the highly sensitive detection of hydrogen peroxide. As such, hydrogen peroxide may be detected at submillimolar concentrations using the subject stable dry reagent formats, e.g., test strips, where by submillimolar concentration is typically meant concentrations ranging from 0.010 to 1 mM, usually from about 0.050 to 0.8 mM. Use of the subject signal producing systems that include a urea derivative dye provides for more sensitive detection of hydrogen peroxide as compared to signal producing systems that include a dye substrate other than a urea derivative dye, e.g., N-ethyl-N-(2-hydroxy-3-sulfopropyl)-3-methylaniline, 4-aminoantipyrine (see FIG. 3).

In the subject methods, the sample and the signal producing system including a urea derivative dye are combined into a reaction mixture, e.g., by applying the sample to the test strip, the reaction is allowed to proceed for a sufficient period to time to generate a signal indicative of the presence (and often the amount) of analyte in the sample, and the resultant signal is detected and related to the presence (and often the amount) of analyte in the sample. The subject methods are now discussed further in terms of methods in which a reagent test strip is employed.

In practicing the subject methods, the first step is to apply a quantity of the physiological sample to the test strip, where the test strip is described supra. The amount of physiological sample, e.g., blood, that is applied to the test strip may vary, but generally ranges from about 2 $\mu$L to 40 $\mu$L, usually from about 5 $\mu$L to 20 $\mu$L. Because of the nature of the subject test strip, the blood sample size that is applied to the test strip may be relatively small, ranging in size from about 2 $\mu$L to 40 $\mu$L, usually from about 5 $\mu$L to 20 $\mu$L. Where blood is the physiological sample, blood samples of a variety of different hematocrits may be assayed with the subject methods, where the hematocrit may range from about 20% to 65%, usually from about 25% to 60%.

Following application of the sample to the test strip, the sample is allowed to react with the members of the signal producing system to produce a detectable product that is present in an amount proportional to the initial amount of the analyte of interest present in the sample. The amount of detectable product, i.e., the signal produced by the signal producing system, is then determined and related to the amount of analyte in the initial sample.

Analyte Detection Systems

Analyte detection systems useful for practicing the subject methods include a reagent test strip and an automated instrument. In such systems, a physiological sample is applied to the test strip as described above and the signal produced by the signal producing system is detected and related to the presence (and often the amount) of analyte in the sample by the automated instrument. The above described reaction, detection and relation steps, and instruments for practicing the same, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,902,731; 5,968,836 and 5,972,294; the disclosures of which are herein incorporated by reference. In the relation step, the derived analyte concentration takes into account the constant contribution of competing reactions to the observed signal, e.g., by calibrating the instrument accordingly.

The subject analyte detection systems include enzyme immunoassay systems for analyte determination, where such systems include multiple test strips forming a strip plate that includes a positively charged porous matrix and a urea derivative dye on at least one surface of the matrix, e.g., an enzyme-linked immunosorbent assay (ELISA) where the enzyme is a peroxidase and the strip plate further includes an analyte-specific antibody on at least one surface of the matrix.

Kits

Also provided by the subject invention are kits for use in practicing the subject methods. The kits of the subject invention include a reagent test strip that includes a peroxide producing signal producing system, as described above, and at least one of a means for obtaining said physiological sample, e.g., a lance for sticking a finger, a lance actuation means, and the like, and an analyte standard, e.g., an analyte control solution that contains a standardized concentration of analyte. In certain embodiments, the kits also include an automated instrument, as described above, for detecting the amount of product produced on the strip following sample application and relating the detected product to the presence (and often the amount) of analyte in the sample. Finally, the kits include instructions for using the subject kit components in the determination of an analyte concentration in a physiological sample. These instructions may be present on one or more of the packaging, a label insert, containers present in the kits, and the like.

The following examples are offered by way of illustration and not by way of limitation.

EXAMPLES

Example 1

Screening of Commercially Available Dye Substrates

The stock solutions of various dyes listed below were prepared in either water or water/0.2M citrate or water/0.2M citrate/ethanol mixture. The concentrations of dye stock solutions ranged from 8 mM to 50 mM. A 10 mg/ml HRP stock solution was also prepared in 0.02M PBS, pH 7.4 solution. Dye/HRP solution was then prepared by mixing the proper volume of dye stock solution, 10 mg/ml HRP stock solution and 0.02M PBS buffer to the final concentration of [HRP]=1 mg/ml and [dye]=1 mM. 200 $\mu$l of the thus prepared dye/HRP was then added to microtiter plate wells, followed by 20 $\mu$l 500 mM $H_2O_2$ solution. The absorbance of the solution was taken by microtiter plate reader after the color development reached steady state (in less 2 min.)

| Dye Substrate | Abbreviation |
|---|---|
| 10-(carboxymethylaminocarbonyl)-3,7-bis(dimethylamino)phenothiazine, sodium salt | DA-67, WAKO's |
| N-(carboxymethylaminocarbonyl)-4,4'-bis(dimethylamino)diphenylamine, sodium salt | DA-64 |
| N-ethyl-N-(2-hydroxy-3-sulfopropyl)-3-methoxyaniline | ADOS |
| N-ethyl-N-(3-sulfopropyl)-3-methoxyaniline | ADPS |
| N-ethyl-N-(2-hydroxy-3-sulfopropyl)aniline | ALOS |
| N-ethyl-N-(3-sulfopropyl)aniline | ALPS |
| N-ethyl-N-(3-sulfopropyl)-3-methylaniline | TOPS |
| N-ethyl-N-(2-hydroxy-3-sulfopropyl)-3-methylaniline, sodium salt | TOOS |
| 3,3',5,5'-tetramethylbenzidine, dihydrochloride | TMBZ-HCl |
| N-(3-sulfopropyl)-3,3',5,5'-tetramethylbenzidine | TMBZ-PS |
| 2,2'-azinobis(3-ethylbenzothiazolin-6-sulfonic acid) | ABTS |
| N-ethyl-N-(3-sulfopropyl)-3,5-dimethylaniline | MAPS |
| bis(4-[N-ethyl-N-(3'-sulfopropyl)-amino-2,6- | Bis-MAPS-C2 |
| bis(4-[N-propyl-N-(3'-sulfopropyl)-amino-2,6- | Bis-MAPS-C3 |
| bis(4-[N-butyl-N-(3'-sulfopropyl)-amino-2,6- | Bis-MAPS-C4 |
| N,N-bis(2-hydroxy-3-sulfopropyl)tolidine | SAT |
| N,N-bis(4-sulfobutyl)-3,5-dimethylaniline | MADB |
| N-ethyl-N-(2-hydroxy-3-sulfopropyl)-3,5-dimethylaniline | MAOS |

Example 2

Preparation of Test Strips Coated with a Peroxide Producing Signal Producing System Including DA-67

A ONE-TOUCH® Nylon membrane was cut into strips of ¼" wide and 12" long, and the membrane strip was first coated with the A dip solution and then with the B dip solution (ingredient and concentration specified in the following table). After each coating, the membrane was dried in hot air oven for 10 minutes at 55° C. The coated membrane was stuck to a 2"×12" MELINEX® support (a polyester film or sheet made by Du Pont), which has a 5 mm diameter circular hole opening every quarter inch along its length for color measurement. The MELiNEX® support also has two stripes of ⅜" wide adhesive printed on top and bottom of holes. The membrane was laminated in the way that it completely covers the holes on the MELINEX® support. A layer of sample-spreading POREX™ material (a norous high density polyethylene material made by Porex Corp.) (1"×12") was further laminated on top of membrane by adhesive printed on MELINEX® support. The whole assembly was then cut into ¼ " wide strips.

| Ingredient | Concentration |
|---|---|
| A dip formulation | |
| Ketoamine oxidase | 206 U/ml |
| Horseradish peroxidase | 1 mg/ml |
| Mannitol | 4% |
| Poly(vinylpyrrolidone) (PVP), MW = 360K | 1% |
| EDTA | 5 mM |
| buffer | 0.1 M sodium phosphate |
| pH | 7.5 |
| B dip formulation | |
| DA-67 | 1.5 mM |
| solvent | 70% methanol |

Example 3

Detection of Hydrogen Peroxide

To demonstrate the feasibility of color development on strips coated with stabilized DA-67 dye, a ONE-TOUCH® Nylon membrane was coated with a solution containing 2.5 mM DA-67, 1 mg/ml HRP and 1% PVP (MW=360K) in 0.5 M pH 8.0 phosphate buffer. The membrane was then stuck to MELINEX® support, covered with POREX™ material and cut into testing strips as described in example 2. Ten µL volumes of various concentrations of $H_2O_2$ solutions were dropped on the strips respectively, and the color formation was monitored using a MACBETH REFLECTOMETER™ (an instrument for measuring color by means of reflectance spectroscopy made by GretagMacbeth Corp.). To compare the detection sensitivity of DA-67 dye with that of the most commonly used dye for $H_2O_2$, TOOS-4 AP, a ONE-TOUCH® Nylon membrane was coated with a solution containing 5 mM TOOS, 5 mM 4 AP, 1 mg/ml HRP and 1% PVP (MW=360K) in 0.02 M PBS, pH 7.4. The membrane was then used to prepare test strips as described in example 2 and tested with $H_2O_2$ by the way DA-67 coated strips was tested. The results were plotted in figure 3.

It is evident from the above results and discussion that the subject invention provides for the significant stabilization of a highly sensitive urea derivative dye member of a hydrogen peroxide based signal producing system useful for analyte detection. As such, the subject invention provides for more sensitive analyte detection, as compared to certain prior art compositions and methods, e.g., ones that rely on dye substrates other than urea derivative dyes, and represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A reagent test strip for use in detecting the presence or determining the concentration of an analyte in a physiological sample, said strip comprising:

a positively charged porous matrix; and a peroxide producing signal producing system present on said matrix, wherein said peroxide producing signal producing system includes a urea derivative dye.

2. The composition according to claim 1, wherein said positively charged porous matrix comprises nylon.

3. The composition according to claim 1, wherein said urea derivative dye is negatively charged.

* * * * *